United States Patent [19]

Knöfel et al.

[11] Patent Number: 4,879,408
[45] Date of Patent: Nov. 7, 1989

[54] CYCLOALIPHATIC DIISOCYANATES OPTIONALLY IN THE FORM OF ISOMER MIXTURES AND A PROCESS FOR THEIR PRODUCTION

[75] Inventors: Hartmut Knöfel, Odenthal-Erberich; Michael Brockelt, Bergisch-Gladbach; Stefan Penninger; Herbert Stutz, both of Dormagen, all of Fed. Rep. of Germany

[73] Assignee: Bayer Aktiengesellschaft, Leverkusen, Fed. Rep. of Germany

[21] Appl. No.: 35,571

[22] Filed: Apr. 7, 1987

Related U.S. Application Data

[63] Continuation of Ser. No. 531,389, Sep. 12, 1983, abandoned.

[30] Foreign Application Priority Data

Sep. 25, 1982 [DE] Fed. Rep. of Germany ....... 3235573

[51] Int. Cl.$^4$ ............................................. C07C 69/00
[52] U.S. Cl. .................................................... 560/330
[58] Field of Search ......................................... 560/330

[56] References Cited

U.S. PATENT DOCUMENTS 3,361,814 1/1968 Campbell .
3,565,768 2/1971 Grant .
3,870,683 3/1975 Freure .

Primary Examiner—Alan Siegel
Attorney, Agent, or Firm—Gene Harsh; Joseph C. Gil

[57] ABSTRACT

Diisocyanates and isomer mixtures of diisocyanates corresponding to the formula

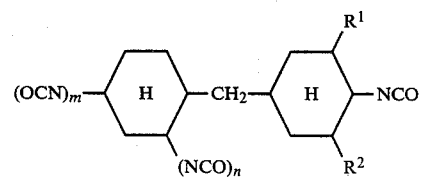

in which $R^1$, $R^2$, m and n are as defined herein are produced by phosgenating diamines and isomer mixtures of diamines corresponding to the formula

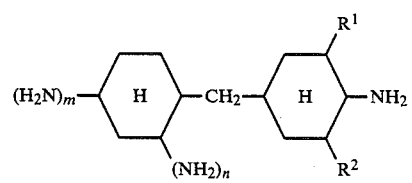

in which $R^1$, $R^2$, m and n are as defined herein. These diisocyanates which are liquid at room temperature and highly compatible with polyols are particularly useful in the production of polyurethanes.

5 Claims, No Drawings

CYCLOALIPHATIC DIISOCYANATES OPTIONALLY IN THE FORM OF ISOMER MIXTURES AND A PROCESS FOR THEIR PRODUCTION

This application is a continuation of application Ser. No. 531,389, filed Sept. 12, 1983, abandoned.

BACKGROUND OF THE INVENTION

This invention relates to new methylene-bis(cyclohexylisocyanates) monosubstituted on only one cyclohexane ring and to a process for their production.

Aliphatic or cycloaliphatic diisocyanates, such as hexamethylene diisocyanate, 3,5,5-trimethyl-1-isocyanato-3-isocyanatomethyl cyclohexane and 4,4'-methylene-bis-(cyclohexylisocyanate), and their position and/or stereo-isomer mixtures are used in polyurethane chemistry. Such diisocyanates are useful in the production of light-stable coating materials characterized by high resistance to weathering. In addition, isomer mixtures of such diisocyanates may be readily processed by reaction with polyols to form lacquer binders, elastomers, or foams provided that the diisocyanate is liquid at room temperature and compatible or adequately miscible with the polyols (See for example, German Offenlegungsschrift No. 1,768,832). Pure trans, trans-4,4'-methylene-bis-(cyclohexylisocyanate), for example, is not suitable for such processes because it is solid at room temperature (melting point 83° C.) and is sparingly soluble in polyols. It is therefore removed from the reaction mixture by crystallization before the end of the polyaddition reaction.

The stereo-isomer mixture consisting of trans, trans-, cis, trans- and cis, cis-4,4'-methylene-bis(cyclohexylisocyanate) which is formed in the phosgenation of nucleus-hydrogenated 4,4'-diaminodiphenyl methane is also solid at room temperature. Because the trans, trans-diamine is obtained as the main product where hydrogenation is carried out under normal conditions, this stereoisomer mixture can be used only to a limited extent for producing polyurethanes.

Although the separation of trans, trans-4,4'-methylene-bis-(cyclohexylisocyanate) from the stereoisomer mixture is technically possible, for example by precipitating the trans, trans-isomer in the form of carbamic acid chloride, followed by filtration (See Japanese Patent Publication No. 53 046-944 of Apr. 27, 1978), the yield of isocyanate is regarded as a major disadvantage.

It is known that liquid cycloaliphatic diisocyanates can be obtained by the phosgenation of 2,4'-methylene-bis-(cyclohexylisocyanate) (See German Offenlegungsschrift No. 1,768,832). According to this publication, mixtures of 2,4'- and 4,4'-isomers are even liquid when the 2,4'-isomer content amounts to between 30 and 95 wt. % and the 4,4'-isomer has a trans, transisomer content of less than 50 wt. %. However, the 2,4'-isomer is difficult to obtain in pure form because it is obtained in 3 stages (by the condensation of aniline with formaldehyde, followed by nucleus hydrogenation and phosgenation) and 2,4'-diaminodiphenyl methane is obtained in a yield of only about 30% of the theoretical in the condensation stage, even under optimal conditions (See, German Offenlegungsschrift No. 1,937,685) Consequently, isolation of the pure 2,4'-isomer requires technically involved isomer separation.

The direct production of a methylene-bis(cyclohexylisocyanate) rich in 2,4'-isomers by phosgenating a corresponding methylene-bis-(cyclohexylamine)-isomer mixture is also disadvantageous because in the aniline/formaldehyde condensation stage, the 2,4'-diaminodiphenyl methane content correlates to that of the 2,2'-isomer. Further, the 2,2'-isomer undergoes decomposition during the nucleus hydrogenation stage.

SUMMARY OF THE INVENTION

It is an object of the present invention to provide new cycloaliphatic diisocyanates based on methylene-bis-(cyclohexylisocyanate) which are liquid at room temperature, which satisfy practical requirements with respect to solubility and compatibility with polyols and which are not attended by any of the disadvantages of the prior art.

These and other objects which will be apparent to those skilled in the art are accomplished by phosgenating diamines, optionally present in the form of position- and/or stereo-isomer mixtures, corresponding to the formula

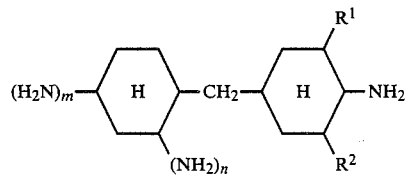

in which $R^1$, $R^2$, m and n are as defined herein to produce diisocyanates corresponding to the formula

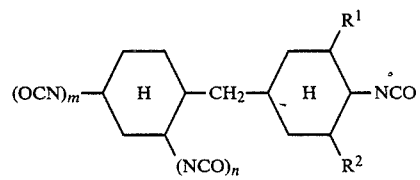

in which $R^1$, $R^2$, m and n are as defined herein.

DETAILED DESCRIPTION OF THE INVENTION

The present invention relates to diisocyanates, optionally in the form of isomer mixtures, corresponding to the general formula

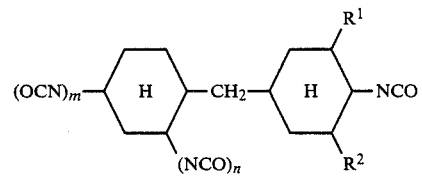

in which $R^1$ and $R^2$ may be the same or different and each represents hydrogen or (optionally branched) $C_1$-$C_{12}$- (preferably $C_1$-$C_4$-) alkyl groups, particularly methyl groups, with the proviso that at least one of the radicals $R^1$ and $R^2$ represents an alkyl radical, and m and n are each 0 or 1, with the proviso that the sum of m+n is 1 and where m or n=0, the free valency remaining is saturated by hydrogen.

The present invention also relates to a process for producing these diisocyanates or diisocyanate mixtures by phosgenating the cycloaliphatic diamines on which the diisocyanates are based and which are optionally present in the form of a position and/or stereoisomer mixture in accordance with techniques known to those in the art.

The present invention also relates to the production of polyurethanes from the new diisocyanates or diisocyanate mixtures by the isocyanate polyaddition process.

Starting materials for the process of the present invention are cycloaliphatic diamines, optionally present in the form of position and/or stereoisomer mixtures, corresponding to the general formula

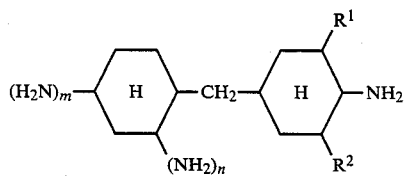

in which
$R^1$ and $R^2$, m and n are as already defined. These diamines are preferably produced by nucleus hydrogenation of the diaminodiphenyl methanes on which they are based.

These asymmetrically substituted diaminodiphenyl methanes may be obtained, for example, by the condensation of o- and/or p-nitrobenzyl halides (particularly chlorides) with substituted anilines

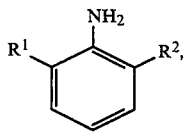

reduction of the nitro groups to the primary amine and subsequent rearrangement in accordance with German Patentschrift No. 864,533 or British Patent No. 1,567,114. Depending upon whether pure o-nitrobenzyl halide, pure p-nitrobenzyl halide or mixtures of these isomers are used in the condensation reaction, the process of the present invention ultimately yields diisocyanates corresponding to the above general formula in the form of pure isomers or isomer mixtures. The ratio of the 4,4'-diisocyanato-3(5)-(di)-alkyl diphenylmethanes to the 4,2'-diisocyanato-3(5)-(di)-alkyl diphenylmethanes largely corresponding to the o-nitrobenzyl halide: p-nitrobenzyl halide isomer ratio used for the condensation reaction. Where monosubstituted anilines ($R^2$=H) are used, small quantities (up to 5 Wt. %, base on the mixture as a whole) of 2,4'-diisocyanato-3-alkyl diphenyl methanes and/or of the corresponding 2,2'-isomer are formed via the intermediate stage of the corresponding diamines.

In general, the nucleus hydrogenation of the aromatic diamines is carried out by any of the known methods (See, P. Rylander, Catalytic Hydrogenation in Organic Syntheses, Academic Press, New York/San Francisco/London (1979), page 190), with the aromatic diamines being catalytically hydrogenated until all the hydrogen has been taken up. The hydrogenation reaction is generally carried out at 20° to 300° C. under a pressure of from 20° to 300 bar and preferably at a temperature of from 100° to 300° C. (more particularly in the range from 150° to 250° C.) and under a pressure of from 70 to 300 bar (more particularly, under a pressure of from 120 to 250 bar).

The hydrogenation reaction may be carried out in the presence of from 0.1 to 30 wt. % preferably from 0.1 to 10 wt. % (based on catalytically active metal and diamino compound) of a hydrogenation catalyst. Suitable catalysts include elements of the 8th Secondary Group of the Periodic System of Elements or catalytically active inorganic compounds of these elements, optionally applied to inert supports (such as active carbon, silica gel and, in particular, aluminum oxide). Particularly suitable catalysts are, for example, ruthenium, platinum, rhodium, nickel and/or cobalt catalysts in elemental or chemically bound form. It is particularly preferred to use ruthenium or catalytically active ruthenium compounds. Specific examples of suitable ruthenium compounds are ruthenium dioxide; ruthenium tetroxide; barium perruthenite; sodium, potassium, silver, calcium or magnesium ruthenate; sodium perruthenate; ruthenium pentafluoride; ruthenium tetrafluoride hydrate and ruthenium trichloride. Where supports are used for the catalysts, the metal content of the supported catalyst generally amounts to between 1 and 10 wt. % and, preferably to between 1 and 5 wt. %. The type and quantity of catalyst used are not, however, critical to the present invention.

It is often best to carry out the hydrogenation reaction in the presence of ammonia because ammonia suppresses undesirable deamination reactions and the formation of secondary amines as by-products. If ammonia is used, it is generally employed in quantities of from 0.1 to 30 wt. % and preferably in quantities of from 5 to 10 wt. % (based on the starting materials to be hydrogenated).

The hydrogenation reaction may be carried out in the absence of solvents or in the presence of inert solvents. In general, low-melting or liquid aromatic diamines are hydrogenated as such (i.e., without a solvent) whereas high-melting diamines are hydrogenated in solution. Suitable solvents are low-boiling organic compounds which are inert under the reaction conditions, preferably alcohols (such as methanol, ethanol, n-propanol, i-propanol), or ethers (such as dioxane, tetrahydrofuran and diethyl ether) or hydrocarbons (such as cyclohexane). The hydrogenation reaction may be carried out continuously in a reaction tube, in a cascade of pressure vessels or, preferably, in batches in a stirrer-equipped autoclave. In a batch process carried out in a stirrer-equipped autoclave, the autoclave is filled with catalyst, the substance to be hydrogenated and, optionally, a solvent, repeatedly purged with an inert gas and ammonia optionally introduced. Hydrogen is then introduced under pressure, the mixture heated to the reaction temperature, hydrogenated until a constant pressure prevails and stirred for about another 0.5 to 5 hours at the same temperature. After the reaction mixture has cooled and the catalyst has been separated off, the hydrogenation product is generally worked up by distillation.

The hydrogenation products are obtained in high yields, generally exceeding 90% of the theoretical, and may be freed from secondary products, such as aminoalkyl benzyl cyclohexylamine by distillation. These hydrogenation products are generally stereoisomer mixtures and, in some cases, even position isomer mixtures which largely correspond to the starting materials. Separation into individual position and/or stereoisomers is generally not necessary where the hydrogenation products are to be used as starting materials for the process of the present invention because isomer purity is not important to the process of the present invention. In fact, isomer mixtures are frequently desirable because they improve the properties of the diisocyanates.

Preferred starting materials for use in the process of the present invention which may be obtained by the hydrogenation process described above are, for example, 4,4'-diamino-3,5-dimethyl dicyclohexyl methane, 4,4'-diamino-3,5-diethyl dicyclohexyl methane, 4,4'-diamino-3,5-diisopropyl dicyclohexyl methane, 4,4'-diamino-3-ethyl-5-methyl dicyclohexyl methane and isomer mixtures containing these diamines as their main component; 4,2'-diamino-3,5-dimethyl dicyclohexyl methane, 4,2'-diamino-3,5-diethyl dicyclohexyl methane, 4,2'-diamino-3,5-diisopropyl dicyclohexyl methane, 4,2'-diamino-3-ethyl-5-methyl dicyclohexyl methane and isomer mixtures containing these diamines as their main components; 4,4'-diamino-3-methyl dicyclohexyl methane, 4,4'-diamino-3-ethyl dicyclohexyl methane, 4,4'-diamino-3-isopropyl dicyclohexyl methane and mixtures thereof with other position isomers, such as the corresponding 4,2'-diamino-3-alkyl diphenyl methanes and/or 2,4'-diamino-3-alkyl diphenyl methanes, 4,2'-diamino-3-methyl dicyclohexyl methane, 4,2'-diamino-3-ethyl dicyclohexyl methane, 4,2'-diamino-3-isopropyl dicyclohexyl methane and mixtures thereof with the corresponding 4,4'-diamino-3-alkyl or 2,4'-diamino-3-alkyl dicyclohexyl methanes.

In the process of the present invention for producing the new diisocyanates, the diamines mentioned by way of example or their salts may be phosgenated by any of the methods known to those in the art in the presence of an inert organic solvent (See, Houben-Weyl, Methoden der Organischen Chemie, Georg Thieme Verlag, Stuttgart (1952), Vol. 8, 4th Edition, pages 120 et seq.).

Preferred salts for phosgenation are the hydrochlorides or ammonium carbamates obtained by saturation of the diamine solutions with gaseous hydrogen chloride or carbon dioxide. In principle, it is also possible to phosgenate other salts of the type obtained, for example, by neutralization of the diamines with proton-yielding acids.

The selectivity of the phosgenation reaction is largely dependent upon the concentration of amine and upon the excess of phosgene. The phosgene is preferably used in a large molar excess and the diamine to be phosgenated in highly dilute form. In general, the molar excess of phosgene amounts to between 100 and 2000% and preferably to between 100 and 1000%. The concentration of amine in the amine solution to be phosgenated generally amounts to between 0.1 and 15 wt. % and preferably to between 5 and 10 wt. %.

Suitable solvents are any inert organic liquids or mixtures thereof having a boiling point in the range from 60° to 250° C., i.e. halogenated hydrocarbons, aromatics, hydroaromatics and their chlorine compounds. Examples of suitable solvents are xylene, mesitylene, chlorobenzene, dichlorobenzene, trichlorobenzene, chloronaphthalene and dichloroethane.

The reaction may be carried out either in a single stage by hot phosgenation at temperatures in the range from 100° to 250° C. or in two stages by cold/hot phosgenation under normal pressure at temperatures in the range from −20° to 250° C.

Where the free amines are used as the starting compound (base phosgenation), ammonium carbamic acid chloride is initially prepared at temperatures in the range from −20° to +60° C. and then further reacted with phosgene at temperatures in the range from 20° to 250° C. to form the diisocyanate.

In one preferred embodiment of the process, the amines are dissolved in a suitable organic solvent, precipitated in the form of ammonium carbamates by the introduction of carbon dioxide and the resulting suspension treated with the theoretical quantity of phosgene at temperatures in the range from 0° to 50° C. The temperature is then slowly increased while more phosgene is introduced until a clear solution is formed at temperatures in the range from 100° to 180° C.

The end products of the process may be purified after dephosgenation by evaporation of the solvent, followed by distillation under reduced pressure.

The diisocyanates of the present invention are obtained in high yields in the form of colorless, low-viscosity liquids and are valuable synthesis components in the production of polyurethane plastics by the isocyanate polyaddition process. The position and/or stereoisomerism of the new diisocyanates corresponds to the isomerism of the diamines used in the phosgenation reaction. In general, there is no need for the mixtures accumulating in the process of the present invention to be separated into individual position and/or stereoisomers because the products of the process of the invention may be used directly. This is one of the main advantage of the diisocyanates or diisocyanate mixtures of the present invention over the unsubstituted methylene-bis(cyclohexylisocyanates) of the prior art. These new diisocyanates may be used instead of or together with known polyisocyanates for the production of polyurethane lacquers, polyurethane elastomers or polyurethane foams by known processes.

The invention is further illustrated by the following Examples in which all the percentages quoted represent percentages by weight, unless otherwise indicated.

EXAMPLES

EXAMPLE 1

(1a) In a 0.7 liter fine steel autoclave, 250 g (1.18 mole) of 4,4'-diamino-3-methyl diphenyl methane were hydrogenated for 4 hours at 180° C./200 bar in the presence of 25 g of $Ru/Al_2O_3$-supported catalyst (5% of Ru) and 25 g of ammonia. After the catalyst had been separated off, the product was pre-purified by flash distillation and subjected to fractional distillation in a Vigreux column. 4,4'-diamino-3-methyl dicyclohexyl methane boiling at 110° to 112° C./0.3 mbar was obtained in a yield of 256.2 g (97% of the theoretical).

(1b) Dry carbon dioxide was introduced at room temperature into a thoroughly stirred solution of 112 g (0.5 mole) of 4,4'-diamino-3-methyl dicyclohexyl methane in 1.4 liters of dried chlorobenzene until no more was taken up. The suspension which formed was cooled to 30° C. and treated with 200 g of phosgene. The temperature rose to 50° C. with a reduction in viscosity. The reaction mixture was then heated to reflux temperature over a period of 2 hours during which 300 g of phosgene were introduced. The reaction mixture was then boiled for another 4 hours while more phosgene was introduced and then for another hour during which nitrogen was introduced. The solvent was then separated off by vacuum distillation and the crude product distilled at 168° to 170° C./0.2–0.4 mbar.

4,4'-diisocyanato-3-methyl dicyclohexyl methane having an NCOcontent of 29.3%, a hydrolyzable chlorine content of 0.06% and a viscosity at 25° C. of 30 mPas was obtained in a yield of 114.6 g (80% of the theoretical).

EXAMPLE 2

(2a) Following the procedure of Example (1a), 250 g (0.98 mole) of 4,4'-diamino-3,5-diethyl diphenyl methane were hydrogenated at 200° C./200 bar in the presence of 25 g of supported ruthenium catalyst and 25 g of ammonia until no more hydrogen was taken up. After cooling to room temperature, the autoclave was vented, the crude product was dissolved in methanol and the catalyst was filtered off. The product was then washed twice with methanol, the solutions were combined and, after evaporation of the solvent, the crude product was distilled at 110°-112° C./0.1 mbar. The yield of 4,4'-diamino-3,5-diethyl dicyclohexyl methane amounted to 236.4 g.

(2b) 133 g (0.5 mole) of the diamine produced in Example (2a) were dissolved in 1.4 liters of dried chlorobenzene followed by the introduction of dry carbon dioxide with intensive stirring until the solution was saturated. A fluorescent deposit was formed and the mixture underwent an increase in temperature to 60°-70° C. After cooling to room temperature, the suspension was gassed with 200 g of phosgene and heated slowly to reflux temperature while phosgene was introduced at a rate of 150 g/h. The deposit agglomerated at 65°-70° C. to form a mass which was difficult to stir and which melted slowly above 75° C. The clear solution which formed at 130° C. was phosgenated for another 2 hours, after which the stream of phosgene was stopped and, instead, nitrogen was introduced to remove excess phosgene. Thereafter by 4,4'-diisocyanato-3,5-diethyl dicyclohexyl methane at 162°-165° C./0.3-0.4 mbar. The yield amounted to 140.7 g (87.8% of the theoretical), the NCO-content was 26.2%, the hydrolyzable chlorine was 0.02%, and the viscosity/25° C. was 110 mPas.

EXAMPLE 3

(3a) Following the procedure of Example (1a), 250 g of 4,4'-diamino-3,5-diisopropyl diphenyl methane were hydrogenated at 200° C./200 bar in the presence of 25 g of Ru/Al2O3 catalyst and 25 g of ammonia. After separation of the catalyst and working up by distillation at 141°-144° C./0.1 mbar, 235.3 g of 4,4'-diamino-3, 5-diisopropyl dicyclohexyl methane were obtained.

(3b) 147 g (0.5 mole) of the 4,4'-diamino-3,5-diisopropyl dicyclohexyl methane obtained in Example (3a) were dissolved in 1.4 liters of predried chlorobenzene. Dry carbon dioxide was introduced into the resulting solution at room temperature. After saturation of the suspension formed, 200 g of phosgene were introduced. The reaction mixture underwent an increase in temperature to 60° C. and the deposit agglomerated to form a viscous mass. The solid was melted by rapid heating and by the introduction of more phosgene (150 g/h). A clear solution formed at 125° C. Phosgenation was then continued for another 3 hours under constant conditions, after which the solution was freed from excess phosgene by purging with nitrogen and chlorobenzene was distilled off. The crude product was purified by rapid distillation at 162°-164° C./0.1 m bar. 4,4'-diisocyanato-3, 5-diisopropyl dicyclohexyl methane (NCO-content: 23.6%, hydrolyzable chlorine: 0.03%, viscosity/25° C.: 460 mPas) was obtained in a yield of 158.4 g (96.7% of the theoretical).

EXAMPLE 4

(4a) Following the procedure of Example (1a), 250 g of 4,4'-diamino-3,5-dimethyl diphenyl methane were hydrogenated at 200° C./200 bar in the presence of 25 g of Ru/Al2O3 and 25 g of ammonia. After working up and distillation at 118°-122° C./0.1 mbar, the perhydrogenated starting compound was obtained in a yield of 235.5 g.

(4b) A solution of 119 g (0.5 mole) of 4,4'-diamino-3,5-dimethyl dicyclohexyl methane in 1.4 liters of dry chlorobenzene was saturated with carbon dioxide while stirring. The resulting suspension was treated with 200 g of phosgene at 30° to 50° C. The mixture was then heated to 120° C. over a period of 2 hours, during which phosgene was introduced at a rate of 150 g/h. The deposit passed completely into solution, after which phosgenation was continued for another 3 hours. Thereafter the reaction mixture was dephosgenated for 1 hour, the solvent distilled off and the crude products subjected to flash distillation at 138°-140° C./0.1 mbar. 4,4'-diisocyanato-3,5-dimethyl dicyclohexyl methane (NCOcontent: 28.4%, hydrolyzable chlorine: 0.05%, viscosity/25° C.: 50 mPas) was isolated in a yield of 123.5 g (83.4% of theoretical).

EXAMPLE 5

(5a) Following the procedure of Example (1a), 250 g of 4,4'-diamino-3-ethyl-5-methyl diphenyl methane were hydrogenated in the presence of 25 g of a standard commercial ruthenium catalyst (5% by weight of ruthenium on Al2O3) and 25 g of ammonia. The crude product was taken up in methanol, the catalyst was filtered off, the product washed and the combined solutions were distilled. 251.3 g of 4,4'-diamino-3-ethyl-5-methyl dicyclohexyl methane distilled over at a temperature of 130°-131° C. and under a pressure of 0.1 mbar.

(5b) A solution of 126 g (0.5 mole) of 4,4'-diamino-3-ethyl-5-methyl dicyclohexyl methane in 1.4 liters of chlorobenzene was saturated with dry carbon dioxide and 200 g of phosgene were introduced with intensive stirring at 30° to 50° C. into the suspension formed. The reaction mixture was heated to boiling point while more phosgene was introduced. The solid passed completely into solution and was phosgenated for another 3 hours. Thereafter, the reaction mixture was dephosgenated, the solvent was evaporated off and the crude product was distilled at 145°-147° C./0.05 mbar. 4,4'-diisocyanato-3-ethyl-5-methyl dicyclohexyl methane (NCO-content: 27.1%, hydrolyzable chlorine: 0.03%, viscosity/25° C.: 70 mPas) was obtained in a yield of 129.3 g (83.5% of the theoretical).

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A diisocyanate corresponding to the formula

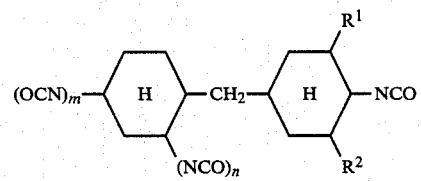

in which

R₁ and R₂ may be the same or different and each radical represents hydrogen or a $C_1$-$C_{12}$-alkyl group, provided that at least one of the radicals $R^1$ and $R^2$ represents an alkyl radical, and m and n each represent 0 or 1, provided that the sum of m+n is 1 and that when m or n represents 0, the free valency is saturated by hydrogen, and in which diisocyanate isomers may be present.

2. The diisocyanate of claim 1 corresponding to the formula

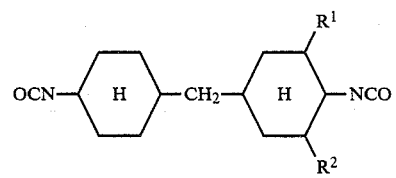

in which $R^1$ and $R^2$ may be the same or different and each represents a $C_1$-$C_4$ alkyl group.

3. The diisocyanate of claim 1 corresponding to the formula

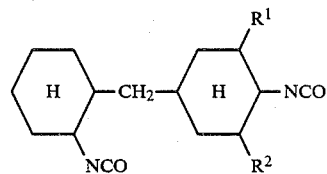

in which $R^1$ and $R^2$ may be the same or different and each represents a $C_1$-$C_4$ alkyl group.

4. The diisocyanate of claim 1 corresponding to the formula

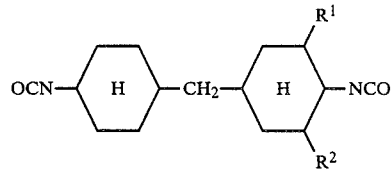

in which $R^1$ represents a $C_1$-$C_4$ alkyl group and $R^2$ represents hydrogen.

5. The diisocyanate of claim 1 corresponding to the formula

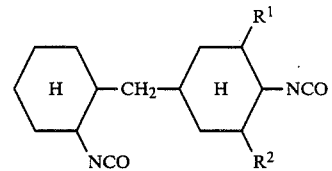

in which $R^1$ represents a $C_1$-$C_4$ alkyl group and $R^2$ represents hydrogen.

* * * * *